(12) United States Patent
Lee et al.

(10) Patent No.: US 8,945,633 B2
(45) Date of Patent: Feb. 3, 2015

(54) **PHARMACEUTICAL COMPOSITION FOR PREVENTING AND TREATING INFLAMMATORY DISEASES CONTAINING AN ETHYL ACETATE FRACTION OF DRIED EXTRACT OF *TRACHELOSPERMI CAULIS* AS AN ACTIVE INGREDIENT, AND METHOD FOR PRODUCING THE FRACTION**

(75) Inventors: Jeong Min Lee, Gunpo-si (KR); Jee Hun Park, Seoul (KR); Jaehoon You, Chungcheongbuk-do (KR); Kyoungmi Noh, Incheon (KR); Sena Kim, Chungcheongbuk-do (KR); Eunsook Ahn, Incheon (KR); Young Suk Lee, Chungcheongnam-do (KR); Young June Lee, Busan (KR); Wahn Soo Choi, Seoul (KR)

(73) Assignee: Shin-IL Pharmaceutical Co., Ltd., Chungcheongbuk-do (KR)

( * ) Notice: Subject to any disclaimer, the term of this patent is extended or adjusted under 35 U.S.C. 154(b) by 782 days.

(21) Appl. No.: 13/120,943

(22) PCT Filed: Sep. 25, 2009

(86) PCT No.: PCT/KR2009/005504
§ 371 (c)(1),
(2), (4) Date: Nov. 10, 2011

(87) PCT Pub. No.: WO2010/036065
PCT Pub. Date: Apr. 1, 2010

(65) Prior Publication Data
US 2012/0308677 A1    Dec. 6, 2012

(51) Int. Cl.
*A61K 36/24*    (2006.01)
*A61K 31/7048*    (2006.01)

(52) U.S. Cl.
CPC ............. *A61K 36/24* (2013.01); *A61K 31/7048* (2013.01); *A61K 2236/39* (2013.01)
USPC .......................................... 424/725; 770/779

(58) Field of Classification Search
CPC ........................... A61K 2300/00; A61K 36/24
USPC ................................................ 424/725, 779
See application file for complete search history.

(56) References Cited

FOREIGN PATENT DOCUMENTS

| CN | 1919856 A | 2/2007 |
|---|---|---|
| KR | 10-0847439 B | 7/2008 |
| WO | WO 2008/091064 A | 7/2008 |

OTHER PUBLICATIONS

The Arthritis Foundation, www.arthritis.org.*
Mu Hong Lee et al. ("In-vitro and in-vivo action of the ethanol extract of *Trachelospermi caulis*" Journal of Pharmacology 2007, vol. 59, No. 1, pp. 123-130).*
Hwang, Man Young et al.: "Inhibition Effect of *Traschelospermi caulis* on the Inflammation and Cell Death in Arthritis", *Korean J Oriental Physiology & Pathology*, 20(2); (2006); pp. 436-441 in Korean with English abstract.
Lee, Mu Hong et al.: "In-vitro and in-vitro anti-inflammatory action of the ethanol extract of *Trachelospermi caulis*"; *Journal of Pharmacy and Pharmacology*, 2007, vol. 59, No. 1, pp. 123-130.
Kang, Hyo Sook et al.: "Anti-inflammatory activity of arctigenin from *Forsythiae fructus*", *Journal of Ethno-Pharmacology*, 116 (2008), pp. 305-312.
Cho, Min Kyung et al.: "Arctigenin, a phenylpropanoid dihenzylbutyrolactonc lignin, inhibits MAP kinases and AP-1 activation via potent MKK inhibition: the role in TNF-α inhibition", *International Immunopharmacology*, 4, (2004), pp. 1419-1429.
Official action issued by Japanese Patent Office for corresponding Japanese application 2011-528943 dated Mar. 27, 2013.
Lee, Mu Hong et al.: "In-vitro and in-vivo anti-inflammatory action of the ethanol extractof *Trachelospermi caulis*", *Journal of Pharmacy and Pharmacology (JPP)*, 2007, pp. 123-130, total 9 pages.
Kang, Hyo Sook et al.: "Anti-inflammatory activity of arctigenin from *Forsythiae fructus*",*Journal of Ethnopharmacology*, 116 (2008) pp. 305-312.
Hwang, Man Young et al.: "Inhibition Effect of *Trachelospermi caulis* on the Inflammation and Cell Death in Arthritis", *Korean Oriental Physiology & Pathology*, 20(2): 2006, pp. 436-441, English abstract only.

* cited by examiner

*Primary Examiner* — Chris R Tate
*Assistant Examiner* — Deborah Davis
(74) *Attorney, Agent, or Firm* — Frommer Lawrence & Haug LLP; Ronald R. Santucci

(57) ABSTRACT

The present invention relates to a pharmaceutical composition for treating and preventing inflammatory diseases comprising an ethyl acetate fraction of dried extract of *Trachelospermi caulis* as an active ingredient and a method for producing the fraction. More particularly, the present invention relates to a composition for preventing and treating inflammatory diseases comprising an ethyl acetate fraction of dried extract of *Trachelospermi caulis* as an active ingredient, in which the extract of *Trachelospermi caulis* is refined and concentrated to contain 0.05~12% by weight of arctigenin as an index material, and a method for producing the fraction.

9 Claims, 12 Drawing Sheets

FIG. 2-a
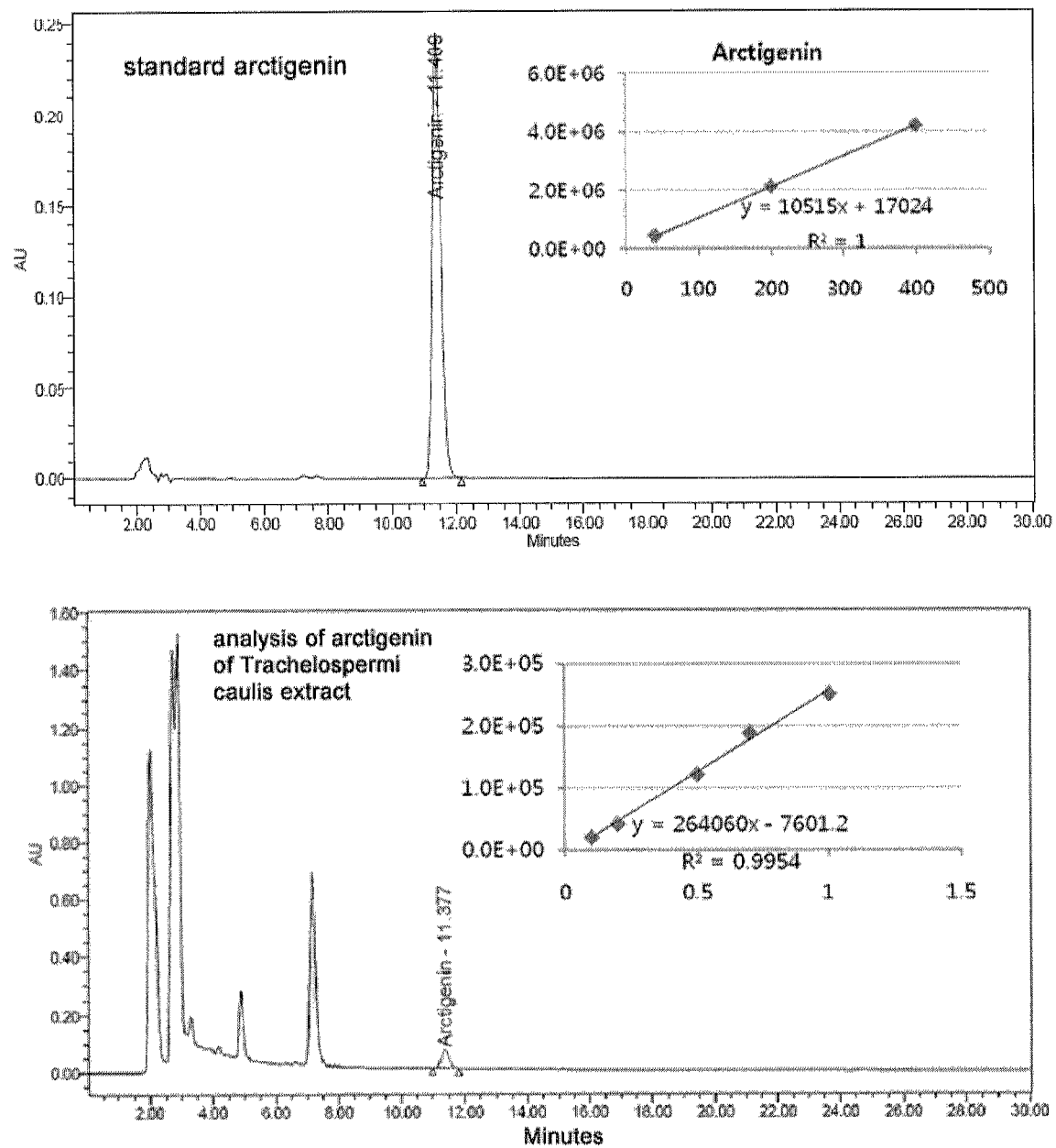

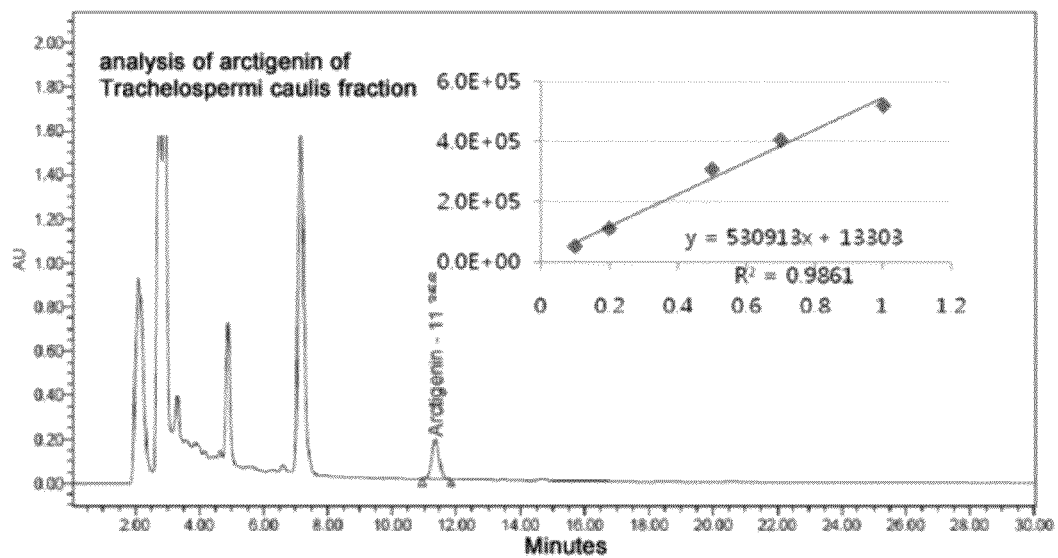
FIG. 2-a cont.

FIG. 2-b
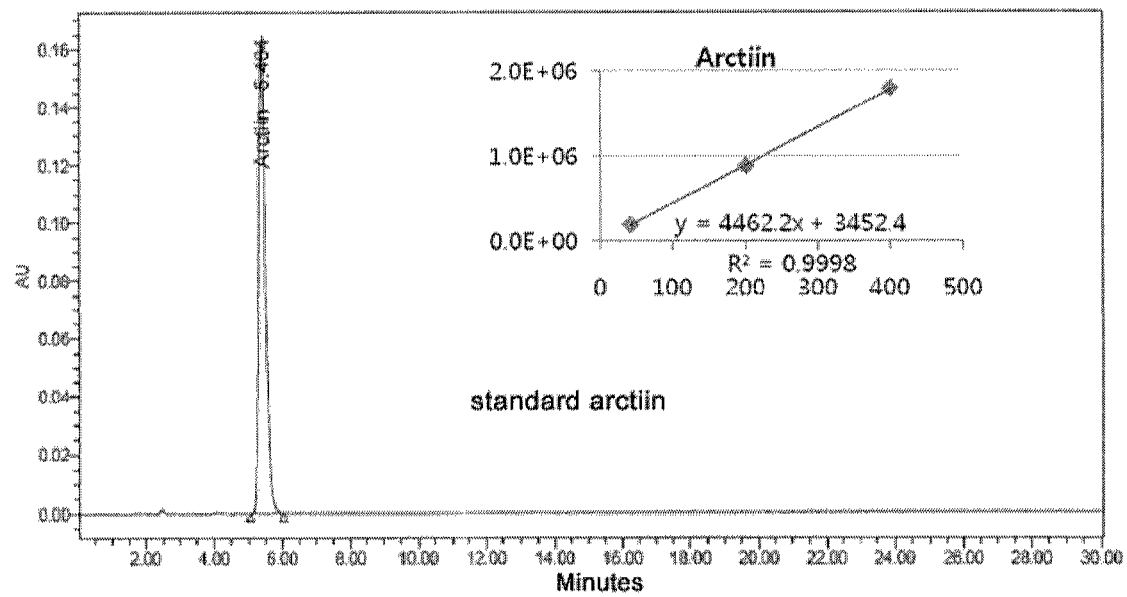
standard arctiin
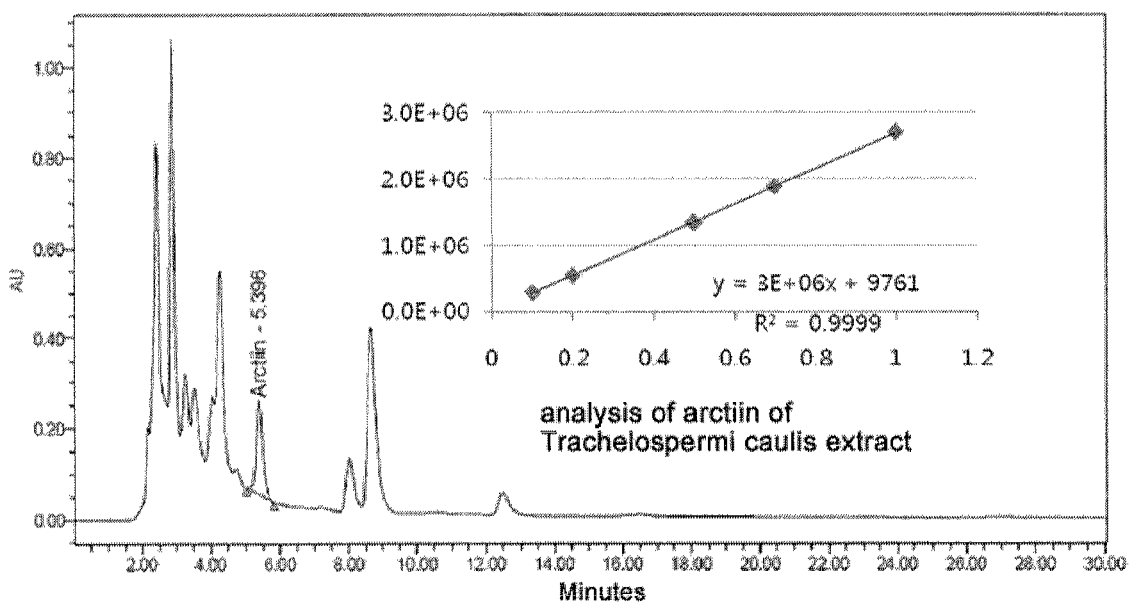
analysis of arctiin of
Trachelospermi caulis extract

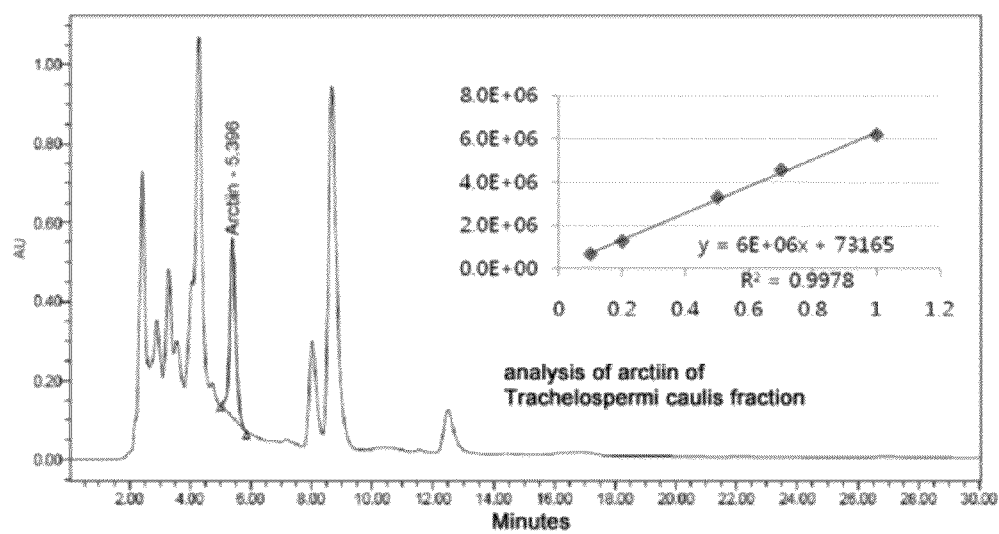
FIG. 2-b cont.

FIG. 3
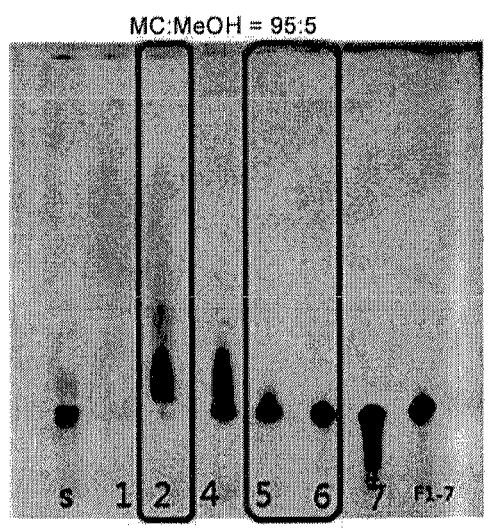
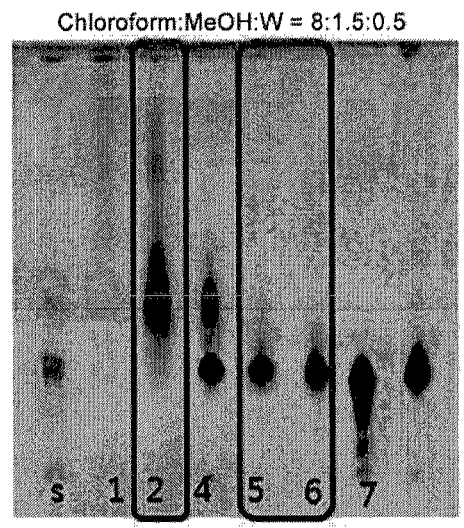

SEQUENCE LISTING

<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggcaactg ttcctgaact caac                                            24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caggacaggt atagattctt tcctttt                                         26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atgaagttcc tctctgcaag agact                                           25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cactaggttt gccgagtaga tctc                                            24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cctcaccatc atcctcactg ca                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcttctctgg gttggcacac ac                                              22

-continued

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaacatcgat gcagccattt                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aggagaaaac gaacatttca                                                 20

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaaggtgaag gtcggagt                                                   18

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gaagatggtg atgggatttc                                                 20

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tttttttttt tttttttt                                                   18
```

PHARMACEUTICAL COMPOSITION FOR PREVENTING AND TREATING INFLAMMATORY DISEASES CONTAINING AN ETHYL ACETATE FRACTION OF DRIED EXTRACT OF *TRACHELOSPERMI CAULIS* AS AN ACTIVE INGREDIENT, AND METHOD FOR PRODUCING THE FRACTION

CROSS-REFERENCE TO RELATED APPLICATION

This application is a 371 of PCT/KR2009/005504 filed on Sep. 25, 2009 published on Apr. 1, 2010 under publication number WO 2010/036065 A which claims priority benefits to Korean Patent Application Number 10-2008-0094224 filed Sep. 25, 2008 and Korean Patent Application Number 10-2009-0090715 filed Sep. 24, 2009, the entire contents of which are incorporated herein by reference.

BACKGROUND (a) Technical Field

The present invention relates to a pharmaceutical composition for preventing and treating inflammatory diseases comprising an ethyl acetate fraction of dried extract of *Trachelospermi caulis* as an active ingredient and a method for producing the fraction.

(b) Background Art

Arthritis is a collective term for a disease associated with inflammatory changes which occur within a joint region due to bacterial infection or external injuries. Arthritis is largely classified into acute arthritis and chronic arthritis, depending on the duration of inflammation.

In this regard, acute arthritis is further divided as follows (Doosan Encyclopedia).

Serous arthritis is generally caused by external injuries, but may occur due to unknown reasons. It usually occurs in one joint.

Serofibrinous arthritis occurs with the acute rheumatoid arthritis, and turbid exudate is gathered in the articular cavity. This may cause dyscinesia even after inflammation is deteriorated due to the generation of pseudomembrane.

Suppurative arthritis occurs in the open wounds of a joint or contagious diseases such as gonorrhea, typhoid, scarlatina, and septicemia. Young infants aged 1-2 months may develop incurable disarticulation due to severe damage on bones. Adults often develop periosteomyelitis which causes purulent discharge to allow release of pus into joints, so called secondary suppurative arthritis.

Chronic arthritis is further divided as follows.

Specific type of inflammation generally refers to tuberculous, syphilitic or gouty arthritis caused by metabolic disorder due to the accumulation of uric acid commonly occurring in middle-aged men. Multiple arthritis is commonly caused by chronic rheumatoid arthritis. It may be developed from acute serous arthritis, may occur as a polyarthritis in the course of tuberculosis, syphilis, and gonorrhea, or may be a kind of septicemia.

In addition, Still's disease also belongs to this category.

Osteoarthritis deformans is generally caused by aging or external injuries of the bones or joints, and hemophilic arthritis is caused by joint bleeding in hemophilia.

There have been developed many pharmaceutical drugs that aim to treat inflammatory diseases represented by the above mentioned arthritis.

*Trachelospermi caulis*, also called as *Trachelospermum asiaticum* var. *intermedium Nakai*, is Lonicera sempervirens which belongs to the family of Apocyanaceae. It grows as high as 5 meters, and has five deeply divided petals. It has strongly scented, pinwheel-shaped white flowers in May-June, and bears fruits around September-November. It has two long fruits that look like a Chinese character representing a person. Surprisingly, the fruits often form a bracelet-shaped, round circle. *Trachelospermi caulis* grows in the seashore, hillside or wilderness in Southern parts of Korea, and generally grows rambling along the rocks, walls, or other trees or plants. In the areas where *Trachelospermi caulis* thrives, other kinds of grasses do not grow, and *Trachelospermi caulis* only covers the area. According to the 'Dictionary of Oriental Medicine' published by North Korea, *Trachelospermi caulis* is dried stems and leaves of *Trachelospermum asiaticum* var. *intermedium Nakai*. It has a bitter taste and a cold property from the viewpoint of oriental medicine. It acts on heart meridian, liver meridian, and renal meridian. It also eliminates wind-dampness and promotes smooth interconnection of meridian pathways. In addition, it is useful to treat paralytic syndrome, cramps of limbs, lumbago, arthritic pains, tonsillitis, and rashes. It is described that about 5-10 g of *Trachelospermi caulis* is decocted and administered orally.

Further, it is used to treat limbs paralysis due to wind-dampness, muscular paralysis, and difficulty in bending and stretching bodies, by blending with dried root bark of *Acanthopanax sessiliflorus* and dried root of *Achyranthes bidentata* BI. It also helps to cool the blood, and thus is decocted and administered for the treatment of sore throat, abscess or the life. The fruits of *Trachelospermi caulis* ripen in July. The ripened fruits are collected and used. 6-12 g is decocted and administered orally to treat bone and muscle aches. Leaves and stems are mostly used, and they are collected any time regardless of seasons, dried in the sunlight, and cut into small pieces before use.

'Chinese Honam medicine paper' recommends that bone and muscle aches are treated by oral administration of *Trachelospermi caulis* prepared by soaking 37-74 g thereof in an alcoholic beverage. 'Kangseo herbal medicine' recommends that arthritis is treated by oral administration of a liquid herbal medicine prepared by decocting each 37 g of *Trachelospermum asiaticum* var. *intermedium Nakai* and *Acanthopanacis Cortex* and 18.5 g of hyssop with water. It is preferable to prepare a liquid herbal medicine by decocting 8-12 g of dried *Trachelospermi caulis* in 200 mL of water until the entire volume is reduced by two-thirds. Alternatively, it can be administered in the form of liquor prepared by soaking it in an alcoholic beverage or in the form of powder. For external use, it is pulverized into powder and then the powder paste is applied to the wounded area. Alternatively, the wounded area is rinsed with the juice of its fresh leaves. *Trachelospermi caulis* is Apocyanaceae that is used to treat lumbago, strengthen bones and muscles, and make joints smooth. *Trachelospermi caulis* has been known to contain tracheloside, arctiin, matairesinoside, arctigenin, notracheloside, etc., as components.

*Trachelospermi caulis* has been described as simple prescription in the old herbal encyclopedia such as Donguibogam, Hyangyakjipsungbang, and Gwangjebigeup, or in the related articles. However, these prescriptions merely mentioned identification by external appearance, efficacies of the oriental herbal medicine, and the preparation methods of decoction. That is, there have been no descriptions of the active ingredients in the extracts of *Trachelospermi caulis*, prepared by the above mentioned methods.

Accordingly, the present inventors obtained Korean Patent No. 0847439 that discloses *Trachelospermi caulis* extract compositions for preventing and treating inflammatory diseases.

However, since natural extracts generally exhibit their efficacy when used in a high dose, and also contain a variety of ingredients, it is difficult to apply them in the preparation of medicines.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art.

It is an object of the present invention to provide a method for producing an ethyl acetate fraction of dried extract of *Trachelospermi caulis*, in which the extract of *Trachelospermi caulis* is refined and concentrated to show the most excellent anti-inflammatory activity.

It is another object of the present invention to provide a pharmaceutical composition for preventing and treating inflammatory diseases, comprising the ethyl acetate fraction of dried extract of *Trachelospermi caulis* as an active ingredient.

In one aspect, the present invention provides a pharmaceutical composition for preventing and treating inflammatory diseases comprising an ethyl acetate fraction of dried extract of *Trachelospermi caulis* as an active ingredient, in which the extract of *Trachelospermi caulis* is refined and concentrated to contain 0.05 to 12% by weight of arctigenin as an index material.

In another aspect, the present invention provides a method for producing an ethyl acetate fraction of dried extract of *Trachelospermi caulis*, comprising the steps of:
(a) dissolving a dried extract of *Trachelospermi caulis* in water, and mixing the solution with ethyl acetate to separate an aqueous layer and an ethyl acetate layer;
(b) separating and recovering the ethyl acetate layer; and
(c) removing a solvent from the recovered ethyl acetate layer, and concentrating the layer to contain 0.05 to 12% by weight of arctigenin as an index material, thereby obtaining a fraction having an anti-inflammatory activity.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein:

FIGS. 2*a* and 2*b* are photographs showing the chromatograms of arctiin and arctigenin of the *Trachelospermi caulis* extract and fraction according to the present invention (Examples 1 and 4);

FIG. 3 is a photograph showing the result of normal-phase chromatography and TLC of the column fractions of the ethyl acetate fraction according to the present invention;

Figure 1:
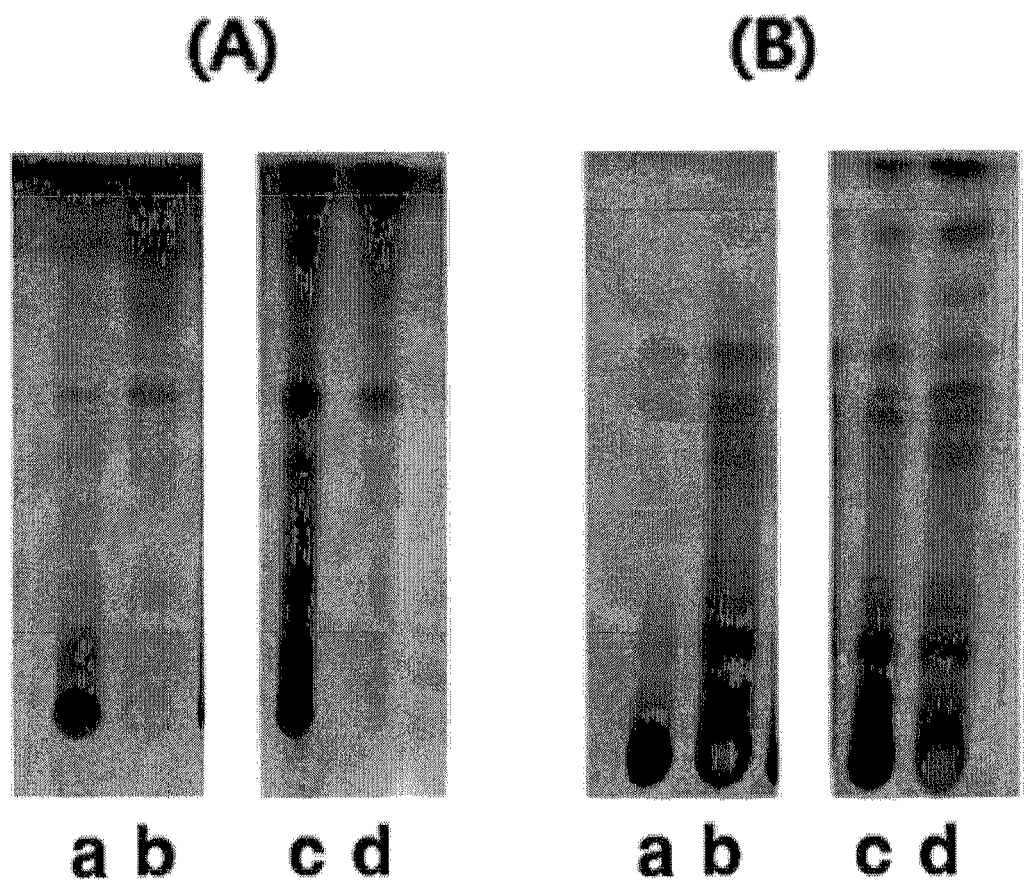
FIG. 1 is a photograph showing the result of TLC patterns of the *Trachelospermi caulis* extracts and fractions according to the present invention [a: Example 2, b: Example 3, c: Example 1, d: Example 4]

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

Hereinafter, the present invention will be described in detail.

Unless defined otherwise, all technical and scientific terms used herein have the same meaning as commonly understood by one of ordinary skill in the art to which this invention belongs.

Further, descriptions of well-known components and processing techniques are omitted so as to not unnecessarily obscure the embodiments of the invention.

The present invention is intended to provide an ethyl acetate fraction of dried extract of *Trachelospermi caulis* (hereinbelow, referred to as ethyl acetate fraction of *Trachelospermi caulis*) that shows more enhanced anti-inflammatory activity than the known dried extract of *Trachelospermi caulis* and a method for producing the same, which can be applied in the preparation of a pharmaceutical composition.

In the present invention, the ethyl acetate fraction of *Trachelospermi caulis* refers to a material that is prepared by adding a solvent to a dried extract of *Trachelospermi caulis*, followed by fractionation and concentration. Herein, the dried extract of *Trachelospermi caulis* refers to a material prepared by extracting *Trachelospermi caulis* with water or an organic solvent and then drying the extract, prior to the fractionation procedure.

In the present invention, the solvent used for the extraction and fractionation of *Trachelospermi caulis* is preferably water or alcohols selected from methanol, ethanol, and butanol, because water and alcohols comply with the requirements of Pharmacopoeia.

In the present invention, it is preferable that chromatography is performed to refine the ethyl acetate fraction of *Trachelospermi caulis*. In particular, it is preferable that chromatography is performed using a polar mobile phase and a non-polar stationary phase or a non-polar mobile phase and a polar stationary phase. More particularly, it is preferable that normal- and reversed-phase chromatography is repeatedly performed to improve refinement.

In the present invention, the normal chromatography employs a silica gel-based stationary, phase, and the reversed-phase chromatography employs ODS (Octa-desyl-silane)-based stationary phase, in particular, C-18 ODS. In this connection, it will be appreciated that a solvent used in the mobile or stationary phase can be readily chosen by those skilled in the art, and thus the specific description will be omitted.

In the present invention, arctigenin is dibenzylbutyroactone ligand having a chemical formula of $C_{21}H_{24}O_6$ and a molecular weight of 372, found in many plants of the family Asteraceae, and its physiological activity has been actively studied. Arctiin, which is glycoside of the arctigenin, has a molecular formula of $C_{27}H_{34}O_{11}$ and a molecular weight of 534, and found in many plants.

The ethyl acetate fraction of dried extract of *Trachelospermi caulis* of the present invention should contain 0.05 to 12% by weight of arctigenin as an index material. If the content is less than 0.05% by weight, the improvement in efficacy is reduced, and if the content is more than 12% by weight, an additional process is needed, and production cost increases, whereas the improvement in efficacy is not sufficient. Therefore, it is preferable that the content of the index material be maintained in the above described range during preparation process. In general, it is more preferable that the fraction is standardized to contain arctigenin of 0.4~3.0% by weight as an index material, in order to reduce production cost and simplify production process. In addition, it is more preferable that the fraction of the present invention contains arctiin of 6~20% by weight as another index material.

The ethyl acetate fraction of *Trachelospermi caulis* that is extracted and refined according to the present invention may be used as it is, but may be prepared into powder, granule, capsule, ointment, transdermal, or injection formulations in admixture with a pharmaceutically acceptable carrier, excipient, diluent or the like. Further, the *Trachelospermi caulis* fraction according to the present invention has long been used as food as well as a drug. Thus, it has no special limit with regard to its dosage, but the dosage may vary depending on the rate of body absorption, body weight, age, sex, health conditions, diet of a patient, administration time, administration method, excretion rate, severity of diseases or the like. In general, it is preferable that the ethyl acetate fraction of *Trachelospermi caulis* is administered at a dose of about 100~1000 mg/day for an adult (60 kg) in terms of efficacy. Since the ethyl acetate fraction of *Trachelospermi caulis* according to the present invention exhibits an excellent efficacy about 20~300% more than the typical extract *Trachelospermi caulis*, the dosage may be determined in consideration of this.

Therefore, the pharmaceutical composition comprising the active ingredient of the present invention should be prepared considering its effective range, and administration of a unit dosage formulation prepared thereby can be monitored, if necessary. Further, a specialized administration method may be used according to the expert's decision and patient's request or it may be administered several times at regular intervals.

In the present invention, inflammatory diseases include acute/chronic inflammatory diseases, rheumatoid inflammatory diseases caused by an autoimmune reaction, degenerative inflammatory diseases or the like.

Hereinafter, a process for refining the extract or fraction of *Trachelospermi caulis* of the present invention will be described.

[First Process] Production Process of Ethyl Acetate Fraction

In this process, the dried extract of *Trachelospermi caulis* is dissolved in water, and ethyl acetate is added to the solution, and mixed with each other to separate an aqueous layer and an ethyl acetate layer.

Thereafter, a solvent is removed from the separated ethyl acetate layer, and the resultant is concentrated to contain arctigenin of 0.05~12% by weight as an index material, thereby obtaining an ethyl acetate fraction having an excellent anti-inflammatory effect.

Extraction efficiency is improved by adding relatively non-polar ethyl acetate to the *Trachelospermi caulis* extract during fractionation.

In the present invention, it is also preferable that the *Trachelospermi caulis* extract is extracted using alcohols during fractionation with ethyl acetate in terms of extraction efficiency and safety. In particular, it is preferable that the *Trachelospermi caulis* extract is extracted with ethanol, methanol, or butanol, and then dried before use, because the use of alcohols in the extraction process increases solubility with water, and active ingredients can be efficiently separated from water during fractionation with ethyl acetate. More particularly, 20~99.9% (v/v) of ethanol is preferred, and 30~95% (v/v) of ethanol is more preferred. If the volume of ethanol is less than 20%, the extraction efficiency of active ingredients is reduced, and if the volume of ethanol is more than 99.9%, production cost increases, whereas the extraction efficiency and efficacy are not sufficiently increased. However, in the present invention, the solvent used for the extraction of *Trachelospermi caulis* extract is not limited to alcohols, and any solvent can be employed as long as it is able to extract a sufficient amount of active ingredients and complies with the requirements of Pharmacopoeia or is safe to the human body.

The following Second and Third Process may be selectively performed according to the efficacy and effective concentration, or physical properties of the extract.

[Second Process] Refining Process

In this process, the ethyl acetate layer separated in First Process is subjected to chromatography to obtain active fractions. In the present invention, normal- or reversed-phase chromatography, or normal- and reversed-phase chromatography is preferably performed to obtain more purified active fractions. In this connection, it will be appreciated that the mobile or stationary phase solvents used in the normal- or reversed-phase chromatography can be readily chosen by those skilled in the art, and thus the specific description will be omitted.

[Third Process] Production Process of Refined Extract

In this process, the active fractions with higher purity prepared by Second Process are dried or concentrated to produce a refined extract.

EXAMPLES

Hereinafter, the present invention will be described in detail with reference to the specific Examples of the present invention. However, the present invention should not be construed as being limited to the Examples set forth her those skilled in the art will appreciate that various modifications and changes are possible, without departing from the scope and spirit of the invention.

Example 1

Preparation of 95% Ethanol Extract of *Trachelospermi caulis*

20 kg of *Trachelospermi caulis* that was washed with purified water and dried was stirred with a 95% ethanol aqueous solution in an amount of about 5~10-times of the herbal medicine, and extracted at about 80° C. for 5 hrs. The extract was slowly cooled to room temperature, and filtered to remove impurities. Then, the filtrates were combined, and concentrated by evaporation of ethanol solvent under reduced pressure to obtain 1 kg of ethanol extract of *Trachelospermi caulis* (yield: about 5%).

Example 2

Preparation of 30% Ethanol Extract of *Trachelospermi caulis*

40 kg of *Trachelospermi caulis* that was washed with purified water and dried was stirred with a 30% ethanol aqueous solution in an amount of about 5~8-times of the herbal medicine, and heat-extracted twice at 2 hr unit. The extract was slowly cooled to room temperature, and filtered by centrifugation to remove impurities. Then, the filtrates were combined, and concentrated at 60~80° C. under reduced pressure.

The concentrate was suspended in the ethanol recovered from the ethanol fraction, and filtered by centrifugation at 1000 rpm. The filtrate was concentrated under reduced pressure, and then dried at 60° C. under the pressure of 0.08 pa, and sterilized during passing through a 80 mesh sieve so as to 1 kg of ethanol extract of *Trachelospermi caulis* in a powder form (yield: about 2.5%).

Example 3

Preparation of Ethyl Acetate Fraction of *Trachelospermi caulis*

100 g of the 30% ethanol extract prepared in Example 2 was dissolved in about 0.8 L of water with stirring, and mixed with an equal amount to two-fold of ethyl acetate (330 mL×5), followed by fractionation to obtain an ethyl acetate-soluble fraction. A suitable amount of sodium thiosulfate (about 125 g) was added to the ethyl acetate-soluble fraction to absorb water molecule of the fraction, and filtered to refine the ethyl acetate-soluble fraction. The refined fraction was concentrated using an aspirator to obtain about 11 g of ethyl acetate fraction of *Trachelospermi caulis*.

Example 4

Preparation of Ethyl Acetate Fraction of *Trachelospermi caulis*

100 g of the 95% ethanol extract prepared in Example 1 was dissolved in about 0.8~2 L of water with stirring, and mixed with an equal amount to two-fold of ethyl acetate, followed by fractionation to obtain an ethyl acetate-soluble fraction. A suitable amount of sodium thiosulfate (about 125 g) was added to the ethyl acetate-soluble fraction to absorb water molecule of the fraction, and filtered to refine the ethyl acetate-soluble fraction. The refined fraction was concentrated using an aspirator to obtain about 16.7 g of ethyl acetate fraction of *Trachelospermi caulis*.

Example 5

TLC Analysis of Ethyl Acetate Fraction of *Trachelospermi caulis*

Each of the extracts and fractions of *Trachelospermi caulis* prepared in Examples 1~4 was dissolved in a small amount of methanol (about 1 mg per 5 mL methanol) and prepared for TLC analysis. Then, the ethyl acetate fraction of *Trachelospermi caulis* in methanol was loaded in silica TLC (normal phase) by spotting using a capillary tube, and dried completely. Thereafter, the fraction was developed in a sealed TLC tank using each different eluent, and the results were detected using a chromogenic agent, shown in FIG. 1 (eluent: (A) ethyl acetate 66%, ethanol 19%, water 15%, (B) chloroform 80%, methanol 15%, water 5%).

As shown in the results, when the ethanol extracts of *Trachelospermi caulis* (a, c) and the ethyl acetate fractions of *Trachelospermi caulis* (b, d) were compared to each other, their starting points in TLC were different from each other. That is, it was clearly observed that the extracts were more refined by the fractionation with ethyl acetate, indicating that the difference in elements separated from the starting point was considerably reduced by fractionation with ethyl acetate, and only a specific portion was refined by fractionation with ethyl acetate.

Example 6

HPLC (High-Performance Liquid Chromatography) Analysis of Index Material of *Trachelospermi caulis*

The contents of index material arctiin in the *Trachelospermi caulis* extract of Example 2 and the *Trachelospermi caulis* fraction of Example 3 were analyzed by high-performance liquid chromatography.

[Arctiin Analysis Conditions]
1) Apparatus: Water HPLC system
2) Eluent: 50% methanol
3) Analysis time: 30 min
3) Flow rate: 1 ml/min
4) Column: YMC-pack Pro C18 RS (250×4.6 mm ID. 5 μm particles)
5) Detector: UV 280 nm
6) Standard arctiin: provided by Hunan Guohua Pharmaceutical Co., Ltd, China The content of arctiin in Example 2 was found to be about 3% by weight, and the content of arctiin in Example 3 was found to change according to fractionation frequency. That is, when ethyl acetate fractionation was performed once, the content was found to be about 19% by weight, which was the highest content. When the fractionation was performed twice to five times, the arctiin contents were found to gradually decrease by about 6% by weight. The ethyl acetate fractions obtained by performing fractionation five times were found to contain about 12~15% by weight of arctiin on the average.

Further, the contents of arctiin and arctigenin in the *Trachelospermi caulis* extract of Example 1 and the *Trach-*

*elospermi caulis* fraction of Example 4 were analyzed by high-performance liquid chromatography. The analysis method of arctiin was performed in the same manner as in Examples 2 and 3, and the analysis of arctigenin was performed as follows.

[Arctigenin Analysis Conditions]
1) Apparatus: Waters HPLC system
2) Eluent: 40% acetonitrile ($CH_3CN$)
3) Analysis time: 30 min
3) Flow rate: 1 ml/min
4) Column: YMC-pack Pro C18 RS (250×4.6 mm ID. 5 μm particles)
5) Detector: UV 280 nm
6) Standard: Sigma-Aldrich catalog No. A1854. (Lot. 074K4701, Germany)

The contents of arctiin and arctigenin in Example 1 were found to be about 2% by weight and 0.5% by weight, respectively. When fractionation was performed three times, the contents of arctiin and arctigenin in Example 4 were found to be about 6% by weight and 1.2% by weight, respectively.

Chromatograms of arctiin and arctigenin were shown in FIG. 2.

Example 7

Normal-Phase Column Chromatography of Ethyl Acetate Fraction of *Trachelospermi caulis*

Active fractions were separated from the ethyl acetate fraction of *Trachelospermi caulis* obtained in Example 3 by silica gel column chromatography using a step gradient solvent system consisting of methylene chloride:methanol (1000:5~95:5).

Briefly, the ethyl acetate fraction of *Trachelospermi caulis* was suspended in about 12-fold of the silica gel in a ratio of methylene chloride:methanol (1000:5) as an eluent, and carefully packed into a glass column. Then, about 10 g of ethyl acetate fraction of *Trachelospermi caulis* was suspended in about 0.5~1-fold of the silica gel, and adsorbed by concentration under reduced pressure, and applied into the column. The fractions were collected in a volume of silica gel column (about 100 ml each) with concentration gradient to methylene chloride:methanol=95:5 in about 5-fold of silica gel volume, and then all fractions were examined by silica gel TLC in the same manner as in Example 5 (see FIG. 3). In this regard, 95% methylene chloride and 5% methanol, or 80% chloroform, 15% methanol and 5% water were used as eluent.

TEST EXAMPLES

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

Test Example

In this Test Example, effects of the extract and fraction on the production of nitric oxide and cytokine were analyzed in order to confirm the anti-inflammatory effect of the fraction according to the present invention. In addition, animal experiment was performed using an arthritis-induced mouse model to analyze the inhibitory effect of the extract on edema and inflammation, and histological staining and analysis on mRNA and protein of arthritis factors were performed using joint tissue samples of animal model.

1. Cell Culture and Refined Extract Treatment

The murine macrophage cell line RAW 264.7 (ATCC, # TIB-71) was cultured using DMEM (Dulbecco's Modified Eagle Medium) supplemented with 10% FBS (fetal bovine serum), penicillin (100 units/ml) and streptomycin sulfate (100 g/ml) at 5% CO2 and 37° C. For each analysis, RAW 264.7 cells were seeded in a 96-well plate at a density of $2 \times 10^4$ cells/well, and after 24 hrs, the cells were stimulated with 300 ng/ml LPS and fractions at various concentrations.

2. Cell Cytotoxicity Test

After incubation for 4 hrs using a TACS XTT Cell Proliferation/Viability Assay kit (R&D systems, Cat. 4891-025-K), cell cytotoxicity was measured at OD 490 nm.

3. Statistical Analysis

Statistical significance for each experimental group was tested as follows. Levene's test was performed on the data obtained from each experimental group to test homogeneity of variance. If homogeneity of variance was obtained, one-way ANOVA was performed. If significance was considered at a level of $p=0.05$, Dunnett's t-test was applied to compare the difference between experimental groups.

Test Example 1

NO Assay

Each culture supernatant was mixed with a Griess reagent (40 mg/ml, Sigma, G4410) at an equal amount (100 μl), and reacted at room temperature for 30 min, and then absorbance was measured at OD 540 nm. The analysis results were represented as % of LPS-stimulated control, $IC_{50}$ (50% inhibitory concentration) value, or inhibition rate, as shown in Tables 1 and 2.

TABLE 1

| Section | $IC_{50}$ (Inhibition of NO production) |
| --- | --- |
| Example 2 | 1180 μg/ml |
| Example 3 | 379.7 μg/ml |

Table 1 shows the comparison of the inhibitory effects of 30% ethanol extract of *Trachelospermi caulis* (Example 2) and ethyl acetate fraction of *Trachelospermi caulis* (Example 3) on NO production, which are represented as $IC_{50}$ value. The resulting 50% inhibitory concentration indicates that the inhibitory effect was improved by fractionation from 1180 μg/ml in Example 2 to 379 μg/ml in Example 3.

In addition, NO inhibition rates of the extract and fraction of *Trachelospermi caulis* (Example 1 and Example 4) were compared to each other in the above method. At the maximum non-cytotoxic concentration 320 μg/ml of Examples 1 and 4, the ethanol extract of Example 1 exhibited a relatively high NO inhibition rate of 68%. As compared with this, the ethyl acetate extract of Example 4 exhibited a higher NO inhibition rate of 80%, indicating more excellent inhibitory effect [Table 2].

TABLE 2

| Section | NO inhibition rate (%) |
| --- | --- |
| Example 1 | 68.1 ± 4.89 |
| Example 4 | 80.3 ± 2.51 |

Test Example 2

Cytokine Analysis

The level of IL-1β or TNF-α present in the culture media was analyzed by ELISA using an IL-1β assay kit (R&D systems, Cat. MLB00B) or TNF-α assay kit (R&D systems, Cat. MTA00). Absorbance was measured at OD 450 nm using a microplate reader. The analysis results were represented as % of LPS-stimulated control.

In this cytokine analysis, the sample treatment concentration was determined on the basis of the non-cytotoxic concentration which was obtained from the cell cytotoxicity test.

The following Table 3 shows the test results of comparison between 30% ethanol extract of *Trachelospermi caulis* (Example 2) and ethyl acetate fraction of *Trachelospermi caulis* (Example 3). The inhibition rates of Example 3 on IL-16 and TNF-α production were 38% and 42%, respectively, indicating higher inhibitory effects than Example 2 [Table 3]. These values were obtained by performing the analysis at the maximum non-cytotoxic concentration (Example 2: 640 μg/ml, Example 3: 160 μg/ml).

TABLE 3

| Section | | IL-1β inhibition rate (%) | TNF-α inhibition rate (%) |
|---|---|---|---|
| Example 2 | | No inhibitory effect | No inhibitory effect |
| Example 3 | | 38% | 42% |
| Example 7 | fraction 2 | 57% | 63% |
| | fraction 5 | 72% | 52% |
| | Fraction 6 | 88% | 35% |

As compared to the ethanol extract of *Trachelospermi caulis*, the ethyl acetate fraction of *Trachelospermi caulis* showed excellent inhibitory effects on inflammatory cytokines, TNF-α and IL-β, implying that the active ingredients were attracted to a more non-polar solvent, ethyl acetate than ethanol, and thus the active ingredients are refined as ethyl acetate-soluble fraction.

Figure 4:
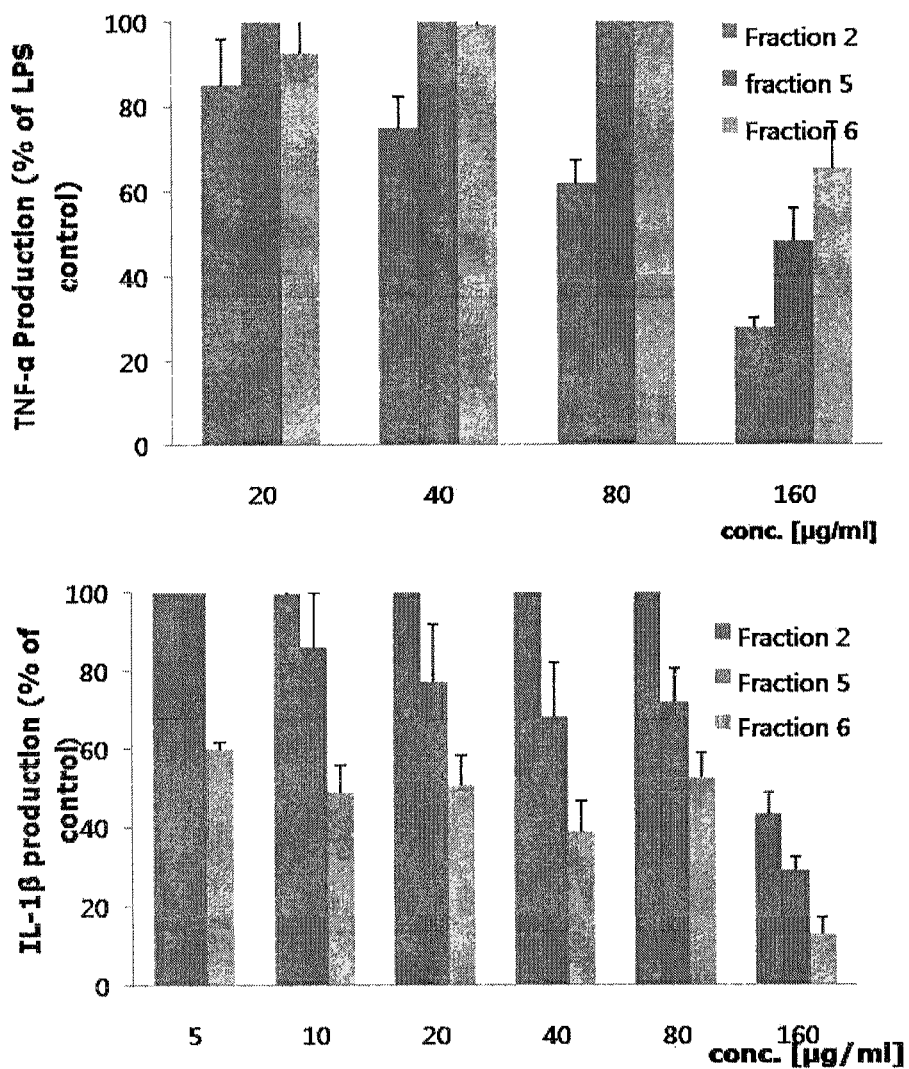
FIG. 4 is a graph showing IL-1β and TNF-α inhibitory activity of the column fractions of the ethyl acetate fraction of *Trachelospermi caulis* according to the present invention.

Furthermore, the cytokines-inhibitory effects of fractions 2, 5, and 6 obtained by an additional refining process of Example 7 were analyzed, and shown in FIG. 4. The fractions exhibited more excellent inhibitory effects on IL-β and TNF-α production even at lower concentrations, indicating that they are more refined forms.

Therefore, it was demonstrated that the fractions according to the present invention have very excellent anti-inflammatory effects in terms of pharmacology, compared to the known extracts.

Test Example 3

Isolation of FLS (Fibroblast-Like Synoviocyte) from Synovial Tissue and Culture The synovial tissue derived from arthritis patient was cut into 1×1×1 mm using scissors, and cultured in HBSS buffer with 1 mg/ml collagenase at 37° C. for 2 hrs. The supernatant was passed through a 70 μm nylon cell strainer (BD, NJ, USA) to isolate cells. The isolated cells were subjected to centrifugation at 1500 rpm for 10 min twice. After removing the supernatant, α-MEM media (10% FBS, 1% L-Glutamine, 1% penicillin-streptomycin) was added to the pellet, and the cells were transferred to a T75-flask, followed by incubation at 37° C. in a $CO_2$ incubator for 2~3 hrs. Then, the cells were washed twice, and cultured. When subculture was performed 3~6 times, 95% or more FLS was obtained (>95% surface markers for fibroblasts (CD90+), <1% CD3+, <1% CD11b, <1% Fcγ Receptor II positive), and used in the experiment.

Test Example 4

Immunoblotting Analysis

Figure 5:
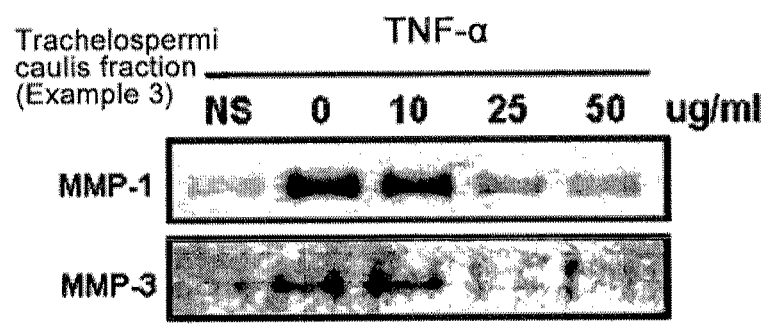
FIG. 5 is a photograph showing a reduction in TNF-α-stimulated MMP-1 and MMP-3 expression in fibroblast-like synoviocytes (FLS) by ethyl acetate fraction of *Trachelospermi caulis* of Example 3 according to the present invention.

FLS obtained in Test Example 3 was aliquoted in a 6-well plate at a density of $2×10^5$/well. After cultivation for 3 days, the culture medium was replaced with incomplete α-MEM (1% L-glutamin, 1% antibiotics), and the cells were treated with the *Trachelospermi caulis* fraction (Example 3) at a concentration of 10, 25, 50 μg/ml. After 30 min, the cells were treated with 20 ng/ml TNF-α. After 24 hrs, each culture medium was separated and extracted. The separated and extracted culture media were subjected to immunoblotting analysis using a 10% SDS-PAGE gel. The effects on FLS-secreted MMP were analyzed using antibodies against MMP-1 and MMP-3, shown in FIG. 5. As shown in FIG. 5, MMP-1 and MMP-3 secretion was significantly reduced by the *Trachelospermi caulis* fraction of Example 3 (10, 25, 50 μg/ml) in a concentration-dependent manner.

Test Example 5

CIA (Collagen-Induced Arthritis) Mouse Model 5-week old male DBA/1J mice were purchased and acclimated for 2 weeks, and then experiment was performed at 7 weeks of age. 100 μg of bovine type II collagen (in 0.05 M acetic acid) was mixed well with an equal amount of Freund's complete adjuvant (Chondrex Inc., Redmond, Wash.), and injected into the tail muscle ($1^{st}$ Immunization). After 21 days, 50 μl (2 mg/ml) of bovine type II collagen was given by intraperitoneal injection (i.p) ($2^{nd}$ Immunization). In the same manner as $2^{nd}$ Immunization, distilled water (vehicle), IND (indomethacin), and *Trachelospermi caulis* fraction (Example 3) were suspended in 5% arabic gum, and orally given daily.

Arthritis score was evaluated by visual examination every three days, which was performed by each examiner (6 persons) in a blind-test fashion.

Figure 6:
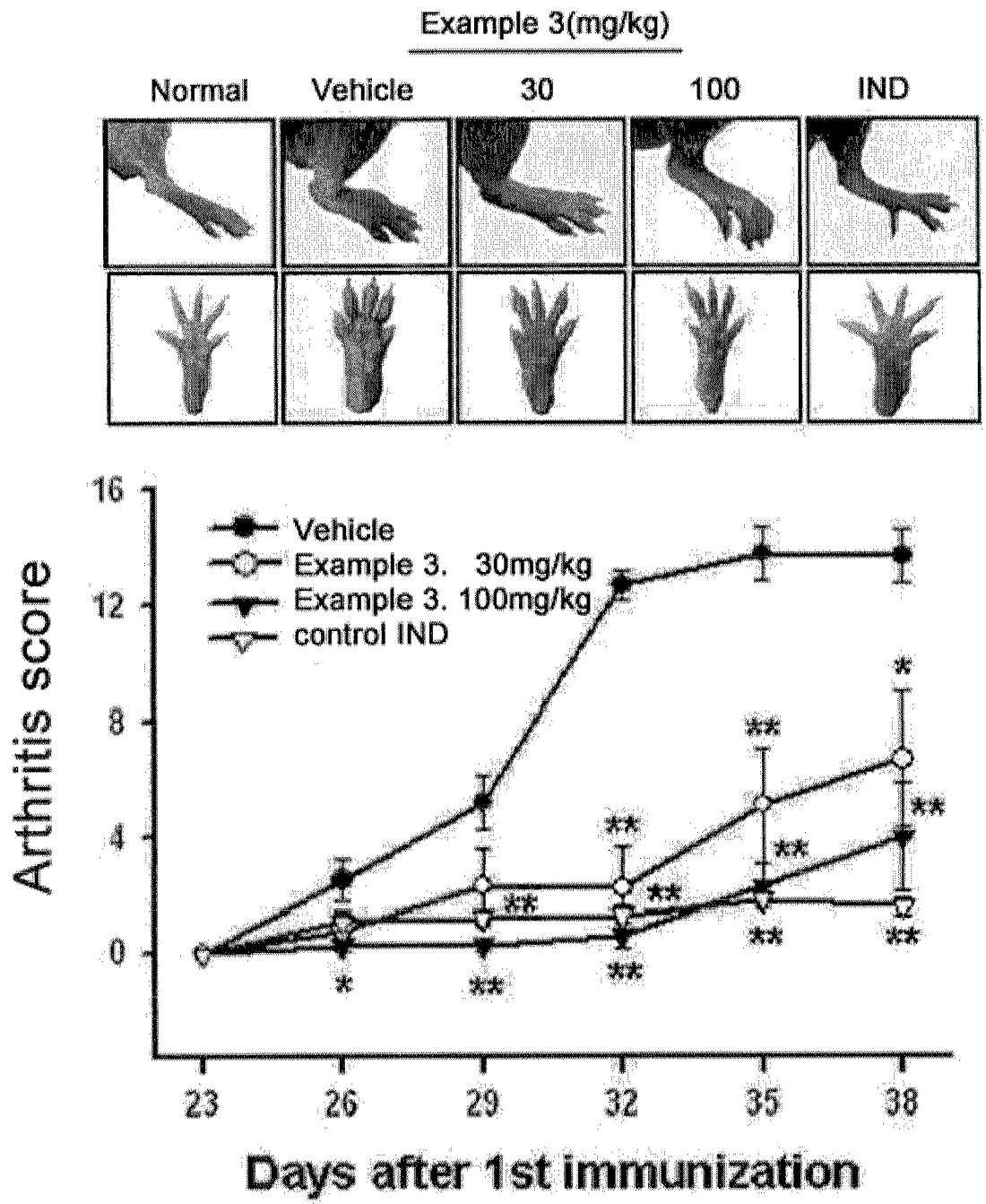
FIG. 6 is a photograph showing the inhibitory effect of *Trachelospermi caulis* fraction (Example 3) on arthritis, which was analyzed by inflammatory edema evaluation using an arthritis-induced mouse model.

Both of the paw and hind leg were assessed, and arthritis was scored according to the following criteria: 0=normal, 1=mild, apparent swelling limited to individual digits, 2=moderate, redness and swelling of the ankle 3=redness and swelling of the paw including digits, and 4=maximally inflamed limb with involvement of multiple joints. The assessment was performed up to 18 days after $2^{nd}$ Immunization. FIG. 6 shows the results of visual examination of CIA.

Figure 7:
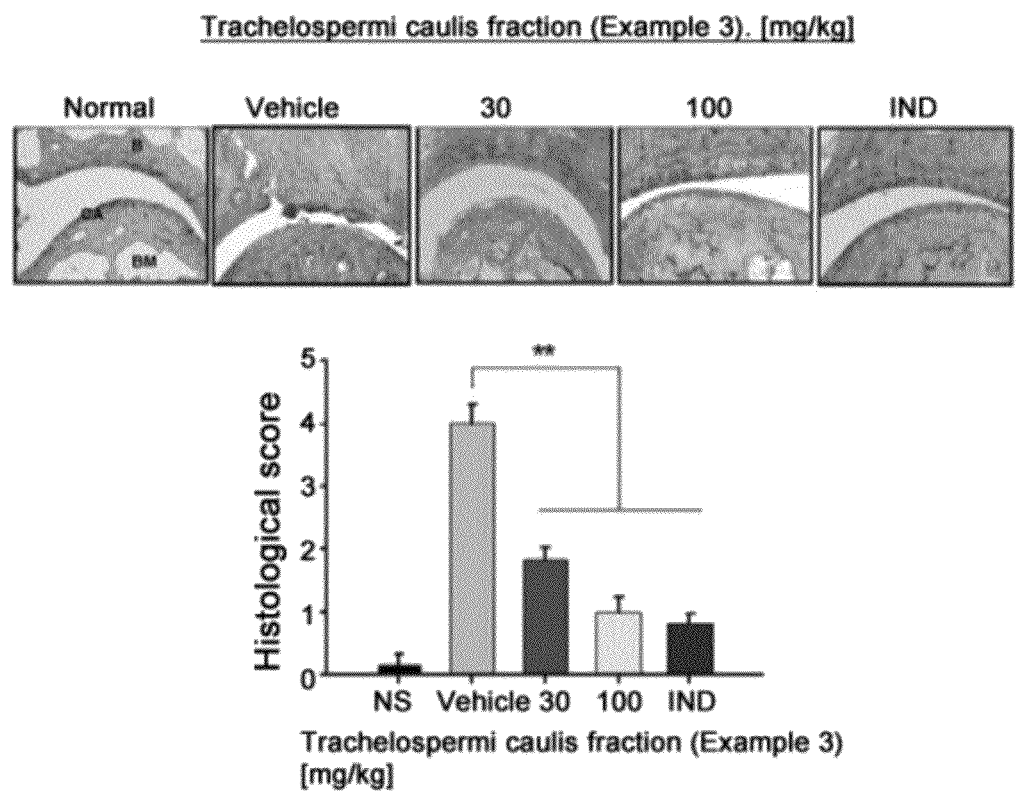
FIG. 7 is a photograph showing the result of H&E staining of the joint of CIA mouse after treatment of *Trachelospermi caulis* fraction (Example 3)

FIG. 7 shows the results of H&E staining of the tissues. 38 days after $1^{st}$ Immunization, CIA animal model was sacrificed, and the hind leg was excised, and fixed in 4% paraformaldehyde (in PBS), followed by decalcification with 10% EDTA, 4% paraformaldehyde (in PBS) for 4 weeks. Then, paraffin sections were prepared in a thickness of 5 μm, and H&E (hematoxylin and eosin) staining was performed to assess cartilage destruction, bone erosion, infiltration of immune cells, pannus formation or the like.

The assessment was performed according to the following criteria: 0=normal, 1=infiltration of immune cells, 2=synovial hyperplasia, pannus formation, 3=bone erosion, destruction. The assessment was performed by 3 or more persons in a blind-test fashion.

Test Example 6 mRNA Extraction and Isolation from Animal Tissue

The tissues of the paw and hind leg collected from CIA animal model (Test Example 5) were frozen in liquid nitrogen, and primarily pulverized using a pestle. Thereafter, total RNA was extracted and isolated using an RNA isolation kit (Intron, Korea). After addition of RNA isolation lysis buffer, vortexing was performed for 30 min, and 200 μl of chloroform was added, followed by centrifugation at 13,000 rpm and 4° C. for 30 min. The supernatant was filtered using an RNA isolation filter to extract total RNA. The extracted and isolated total RNA was quantified using a spectrophotometer (Eppendorf, German).

Test Example 7

RT-PCR (Reverse Transcription-Polymerase Chain Reaction)

Figure 8:
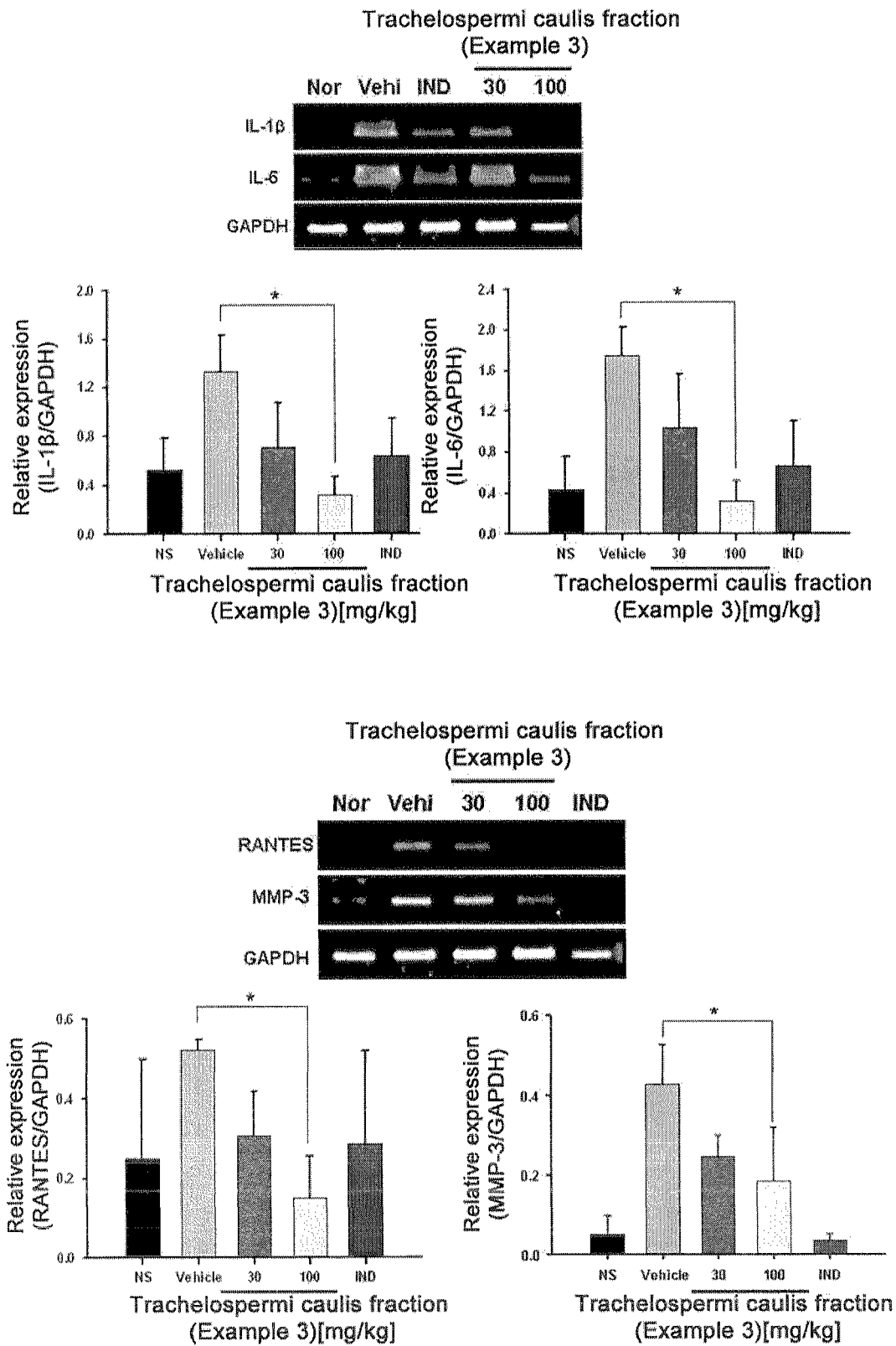
FIG. 8 is a photograph showing the inhibitory effect of *Trachelospermi caulis* fraction (Example 3) on the mRNA expression of IL-1β, IL-6, RANTES, and MMP-3 in the joint tissue of arthritis-induced mouse.

1 μg of total RNA extracted in Test Example 6 was subjected to RT-PCR using a Superscript first strand synthesis system (Invitrogen, CA, USA). 1 μg of total RNA was reacted with Oligo-dT 18mer (SEQ ID NO: 11) (invitrogen, CA, USA) at 72° C. for 5 min, and a reaction buffer mix (3 mM MgCl2, each 0.5 mM dNTP, 5× reaction buffer, 20U ribonuclease inhibitor, and 1 μl of reverse transcriptase) was added thereto. The reaction was performed at 25° C. for 5 min, at 42° C. for 1 hr, and at 72° C. for 5 min. The resulting template was used for PCR. PCR was performed under the following conditions: 33 cycles of at 94° C. for 2 min, at 94° C. for 20 sec, and at 60° C. for 10 sec (RANTES, MMP-3, GAPDH: 50° C.), at 72° C. for 40 sec for IL-1β (IL-6: 35 cycles, RANTES, MMP-3: 35 cycles), finally at 72° C. for 5 min. The resulting product was subjected to electrophoresis in a 2% agarose gel, and stained with ethidium bromide, and then visualized under UV-system. The results are shown in FIG. 8. Each PCR primer sequence is shown in the following Table 4.

TABLE 4

RT-PCR primer sequences

| Section | Sequence |
|---|---|
| IL-1β* | Forward 5-ATGGCAACTGTTCCTGAACTCAAC-3' (SEQ ID NO. 1)<br>Reverse 5'-CAGGACAGGTATAGATTCTTTCCTTT-3' (SEQ ID NO. 2) |
| IL-6* | Forward 5'-ATGAAGTTCCTCTCTGCAAGAGACT-3' (SEQ ID NO. 3)<br>Reverse 5'-CACTAGGTTTGCCGAGTAGATCTC-3 (SEQ ID NO. 4) |
| RANTES | Forward 5'-CCTCACCATCATCCTCACTGCA-3' (SEQ ID NO. 5)<br>Reverse 5'-TCTTCTCTGGGTTGGCACACAC-3' (SEQ ID NO. 6) |
| MMP-3 | Forward 5'-GAACATCGATGCAGCCATTT-3' (SEQ ID NO. 7)<br>Reverse 5-AGGAGAAAACGAACATTTCA-3' (SEQ ID NO. 8) |
| GAPDH | Forward 5'-GAAGGTGAAGGTCGGAGT-3' (SEQ ID NO. 9)<br>Reverse 5'-GAAGATGGTGATGGGATTTC-3' (SEQ ID NO. 10) |

*Molecular Pharmacology. 1997, 52: 30-37.

Test Example 8

Protein Extraction and Isolation from Animal Tissue

The tissues of the paw and hind leg collected from CIA animal model (Test Example 5) were frozen in liquid nitrogen, and primarily pulverized using a pestle. Thereafter, total protein was extracted and isolated using a lysis buffer (20 mM HEPES, pH 7.5, 150 mM NaCl, 1% Nonidet p-40, 10% glycerol, 60 mM octyl β-glucoside, 10 mM NaF, 1 mM Na3VO4, 1 mM phenylmethylsulfonyl fluoride, 2.5 mM nitrophenylphosphate, 0.7 μg/ml pepstatin, and a protease-inhibitor cocktail tablet). The extracted and isolated proteins were quantified by Bradford assay, and analyzed by immunoblotting.

Figure 9:
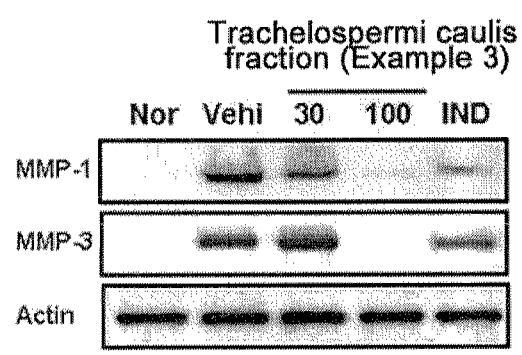
FIG. 9 is a photograph showing the inhibitory effect of *Trachelospermi caulis* fraction (Example 3) on the protein expression of MMP-1, 3 in the joint tissue of an arthritis-induced mouse.

The inhibitory effect of *Trachelospermi caulis* fraction (Example 3) on MMP-1 and MMP-3 expression in the tissues of the paw and hind leg collected from CIA animal model was confirmed in a protein level, shown in FIG. 9.

Preparation Example 1

Preparation of Tablet

For oral administration, tablets with the following composition were prepared using the ethyl acetate fraction of *Trachelospermi caulis* of the present invention by wet granulation and dry granulation methods.

[Composition]

200 mg of ethyl acetate fraction of *Trachelospermi caulis*, 10 mg of light anhydrous silicic acid, 2 mg of magnesium stearate, 50 mg of microcrystalline cellulose, 25 mg of sodium starch glycolate, 101 mg of lactose, 12 mg of povidone, and adequate amount of anhydrous ethanol.

Preparation Example 2

Preparation of Ointment

Ointments with the following composition were prepared using the ethyl acetate fraction of *Trachelospermi caulis* of the present invention.

[Composition]

5 g of ethyl acetate fraction of *Trachelospermi caulis*, 20 g of cetyl palmitate, 40 g of cetanol, 40 g of stearyl alcohol, 80 g of isopropyl myristate, 20 g of sorbitan monostearate, 60 g of polysorbate, 1 g of propyl p-oxybenzoate, 1 g of methyl p-oxybenzoate, and adequate amount of phosphoric acid and sterile water.

Preparation Example 3

Preparation of Injectable Formulation

Injectable formulations with the following composition were prepared using the ethyl acetate fraction of *Trachelospermi caulis* of the present invention.

[Composition]

100 mg of ethyl acetate fraction of *Trachelospermi caulis*, 180 mg of mannitol, 25 mg of sodium phosphate dibasic, 2974 mg of sterile water for injection.

Preparation Example 4

Preparation of Transdermal Formulation

Transdermal formulations with the following composition were prepared using the ethyl acetate fraction of *Trachelospermi caulis* of the present invention.

[Composition]

0.4 g of ethyl acetate fraction of *Trachelospermi caulis*, 1.3 g of sodium polyacrylate 3.6 g of glycerin, 0.004 g of aluminum hydroxide, 0.2 g of methyl parabene, and 14 mL of acrylic adhesive solution.

What is claimed is:

1. A composition for treating inflammatory diseases, comprising an ethyl acetate fraction of dried extract of *Trachelospermi caulis* as an active ingredient, wherein the extract of *Trachelospermi caulis* contains 0.05 to 12% by weight of arctigenin as an index material and 6 to 20% by weight of arctiin.

2. The composition of claim 1, wherein the dried extract of *Trachelospermi caulis* is prepared by extraction with methanol or ethanol and then drying.

3. The composition of claim 1, wherein the dried extract of *Trachelospermi caulis* is prepared by extraction with 20~99.9% (v/v) of ethanol and then drying.

4. A method for producing an ethyl acetate fraction of dried extract of *Trachelospermi caulis*, comprising the steps of:
 (a) dissolving a dried extract of *Trachelospermi caulis* in water, and mixing the solution with ethyl acetate to separate an aqueous layer and an ethyl acetate layer;
 (b) separating and recovering the ethyl acetate layer; and
 (c) removing a solvent from the recovered ethyl acetate layer, and concentrating the layer to contain 0.05 to 12% by weight of arctigenin as an index material, thereby obtaining a fraction having an anti-inflammatory activity.

5. The method of claim 4, wherein the aqueous layer separated in step (a) is mixed with ethyl acetate to separate an aqueous layer and an ethyl acetate layer; the ethyl acetate layer is separated and recovered, and then the separation and recovery steps are repeated 2~5 times, a solvent is removed from the recovered ethyl acetate layer, and concentrated to contain 0.05~12% by weight of arctigenin as an index material, thereby obtaining a fraction having an anti-inflammatory activity.

6. A method of treating inflammatory diseases comprising administering to a subject an effective amount of a composition comprising an ethyl acetate fraction of dried extract of *Trachelospermi caulis* as an active ingredient, wherein the extract of *Trachelospermi caulis* contains 0.05 to 12% by weight of arctigenin as an index material.

7. The method of claim 6, wherein the dried extract of *Trachelospermi caulis* is prepared by extraction with methanol or ethanol and then drying.

8. The method of claim 6, wherein the dried extract of *Trachelospermi caulis* is prepared by extraction with 20~99.9% (v/v) of ethanol and then drying.

9. The method of claim 6, wherein the ethyl acetate fraction of dried extract of *Trachelospermi caulis* comprises 6~20% by weight of arctiin.

\* \* \* \* \*